(12) United States Patent
Springman et al.

(10) Patent No.: US 12,390,354 B2
(45) Date of Patent: Aug. 19, 2025

(54) 3D-PRINTED STRAP CHANNEL FOR AN ORTHOPEDIC OR PROSTHETIC DEVICE

(71) Applicant: Thrive Orthopedics LLC, Indianapolis, IN (US)

(72) Inventors: Michael Springman, Philadelphia, PA (US); Joseph DeHeer, Indianapolis, IN (US); Jari Pallari, Newcastle upon Tyne (GB)

(73) Assignee: Thrive Orthopedics LLC

( * ) Notice: Subject to any disclaimer, the term of this patent is extended or adjusted under 35 U.S.C. 154(b) by 578 days.

(21) Appl. No.: 17/546,466

(22) Filed: Dec. 9, 2021

(65) Prior Publication Data

US 2022/0175569 A1  Jun. 9, 2022

Related U.S. Application Data

(60) Provisional application No. 63/123,097, filed on Dec. 9, 2020.

(51) Int. Cl.
*A61F 5/01* (2006.01)
*B33Y 50/00* (2015.01)
*B33Y 80/00* (2015.01)

(52) U.S. Cl.
CPC ............ *A61F 5/0127* (2013.01); *B33Y 50/00* (2014.12); *B33Y 80/00* (2014.12); *A61F 2005/0132* (2013.01)

(58) Field of Classification Search
CPC .. A61F 5/01; A61F 5/14; A61F 5/0102; A61F 5/0111; A61F 5/0113; A61F 5/0127; A61F 5/0585; A61F 2005/0132; A61F 2005/30943; B33Y 50/00; B33Y 80/00
See application file for complete search history.

(56) References Cited

U.S. PATENT DOCUMENTS

| | | | |
|---|---|---|---|
| 5,431,624 A | 7/1995 | Saxton | |
| 5,897,520 A * | 4/1999 | Gerig | A61F 5/0111 602/65 |
| 5,908,398 A | 6/1999 | Detoro | |
| 6,767,332 B1 | 7/2004 | Pardue | |
| 7,648,472 B2 * | 1/2010 | McCarthy | A61F 5/0111 128/882 |
| 7,662,119 B2 | 2/2010 | DeToro et al. | |

(Continued)

FOREIGN PATENT DOCUMENTS

| | | |
|---|---|---|
| DE | 202017106997 U1 * | 3/2018 |
| DE | 202018106495 U1 * | 1/2019 |
| JP | 2016500017 A * | 1/2016 |

OTHER PUBLICATIONS

Rahm, Mar. 8, 2018, Structural component for protecting and/or supporting a part of the body.*

(Continued)

*Primary Examiner* — Alireza Nia
*Assistant Examiner* — Andrew Jun-Wai Mok
(74) *Attorney, Agent, or Firm* — Tyler B. Droste; Gutwein Law

(57) ABSTRACT

An additive manufactured orthopedic and prosthetic device having a frame with an outer surface and an inner surface. The device includes a channel for a strap member positioned between the outer surface and the inner surface, wherein a bespoke device can be manufactured from 3D printing for supporting an anatomical region of a wearer.

9 Claims, 10 Drawing Sheets

(56) References Cited

U.S. PATENT DOCUMENTS

| | | | |
|---|---|---|---|
| 2006/0217649 A1* | 9/2006 | Rabe | A61F 5/0111 602/65 |
| 2009/0093891 A1* | 4/2009 | Summit | A61F 2/5046 602/3 |
| 2010/0262054 A1* | 10/2010 | Summit | G06F 30/00 700/98 |
| 2014/0180185 A1* | 6/2014 | Zachariasen | G06F 30/00 602/5 |
| 2016/0022466 A1 | 1/2016 | Pedtke | |

OTHER PUBLICATIONS

Summit, Jan. 7, 2016, Orthosis to support the patient's limbs.*
Vogel, Jan. 3, 2019, Orthese.*

* cited by examiner

3D-PRINTED STRAP CHANNEL FOR AN ORTHOPEDIC OR PROSTHETIC DEVICE

CROSS REFERENCE TO RELATED APPLICATIONS

This application claims priority to U.S. Provisional Patent Application No. 63/123,097 filed 9 Dec. 2020 to the above-named inventors and is herein incorporated by reference in its entirety.

FEDERALLY SPONSORED RESEARCH OR DEVELOPMENT

Not Applicable

SEQUENCE LISTING, A TABLE, OR A COMPUTER PROGRAM

Not Applicable

FIELD OF THE INVENTION

The present application relates to the field of medical devices, systems, and methods. More specifically, the technology relates to a series of orthopedic and prosthetic devices, systems, and methods of using the same. More particularly, the present application relates to a series of custom fabricated 3D-printed strap channel devices, systems, and methods of using the devices to treat users.

BACKGROUND

Different types of ankle foot orthosis (AFOs) are designed to target different conditions or deformities by generally supporting or bracing this anatomical area. At this time, the industry standard method for producing such a custom device involves obtaining a cast of the user's anatomy, measurements of the user's anatomy, a 3D scan of the user's anatomy, or a combination of some or all of these methods, for which the brace is being designed. Those user specific casts, scans, and measurements are provided to a company or facility that specializes in fabricating such devices on a bespoke basis. It is an industry standard practice for such devices to be fabricated by hand, utilizing the user's cast in conjunction with such materials as plaster, thermoplastic, carbon fiber, fiberglass and other materials in conjunction with such devices including ovens, autoclaves, vacuums, and others. With the advent and advancement of additive manufacturing, it is now possible, but not yet an industry standard, to have such bespoke devices manufactured from a 3D design file produced from user specific measurements, scans, casts, or a combination of some or all of these or other methods, and subsequently 3D printed for user use.

Relating to both bespoke and prefabricated AFOs and other orthopedic and prosthetic braces and supports, it is common for such devices to utilize hook and loop straps, webbing, D-rings, laces, buckles, and other fastening systems that are secured to the outer or inner surface of the brace by means such as hook and loop or Velcro; metal hardware such as rivets, screws, nuts, and bolts, or sewn onto an external, soft-good or fabric covering that encloses the device. These fastening systems are essential to ensure a secure fit of the device around the user's anatomy.

Securing straps or a fastening system to an external or internal surface of an AFO or orthopedic or prosthetic device by the traditional means mentioned above have the following disadvantages:

Incurrence of additional material costs for items used to secure the straps or fastening system to the device, such as a rivet press, drill, hardware, fabric, soft-goods, hook and loop, glue, and other associated fabrication materials Incurrence of additional labor costs for an individual to fabricate and secure the straps or fastening system to the device using the traditional means referenced above.

In many embodiments, utilizing the traditional means above, straps are secured to a device in a limited number of locations on the surface of the device utilizing such means as rivets or adhesive or glued hook coins. Due to the required length of the strap to secure the device to the user's anatomy and the limited surface area where such attachment points of the strap to the shell are embodied, the strap may tend to hang or droop down from such attachment points when not in use by the user. Straps hanging from the device to the floor may cause additional wear to the straps and may also cause the straps to become soiled and unsanitary. Additionally, because the straps are not adequately held in place on the device at the intended fastening location, it is common for users with dexterity issues to have trouble grabbing, untangling, and fastening the straps. Furthermore, with a conventional strapping or fastening system, where for example a D-ring is attached with a rivet or a screw to an inner or outer body of the device, significant localized stresses are created on the shell material, potentially leading to material failure or breakages.

In certain embodiments, straps or fastening systems secured to an AFO or orthopedic or prosthetic device by the traditional means referenced above, may compromise the appearance aesthetically of the device due to the external and exposed position of the strap/fastening system and/or accompanying hardware or soft goods.

While creating a strap channel or tunnel on a bespoke AFO or orthopedic or prosthetic device via traditional means is possible, it would require tooling and mold costs that are cost prohibitive for such a device to be created on a user-specific and commercially viable basis.

US Patent Application No. 2016/0022466 discloses a series of AFO devices that enables for custom fitting according to a user's needs. This device has a flexible feature that allows for such custom fitting for a foot of a user.

Although a certain degree of personalized fitting can be obtained by utilizing the AFO device of this application, there is still a need for a cost-effective method of fabricating a bespoke device that is fully designed and manufactured according to the user's anatomic characteristics.

BRIEF SUMMARY OF THE INVENTION

The present disclosure aims at overcoming the disadvantages of the traditional methods referred above by developing a 3D-printed strap channel design utilizing the advent and advancement of additive manufacturing design and printing software that allows for a bespoke strap channel to be implemented into the design of an AFO or orthopedic or prosthetic device without incurring the tooling and mold costs associated with the traditional means of implementing such a feature. With the advent and advancement of the present disclosure, it is now possible, but not yet an industry standard, to have such bespoke devices manufactured from a 3D design file produced from user specific measurements, scans, casts, or a combination of some or all of these or other methods, and subsequently 3D printed for user use.

In one aspect of the disclosure, a device defining a strap channel for an ankle foot orthotic (AFO), the device comprising: a frame, the frame comprising an inner surface and an outer surface, wherein the inner surface and the outer surface define at least one strap channel; wherein the at least one channel is between the inner surface and the outer surface, wherein the strap channel is a hollow channel defined between the inner and the outer surfaces of the frame; wherein at least one strap can be threaded through the at least one channel, wherein the channel is continuous from a first side of the frame to a second side of the frame, wherein the first side of the frame to the second side of the frame defines a semi-curvature designed to hold a user's part of the body, wherein the strap channel device is 3D-printed and designed according to a user's anatomic characteristics. A logo may be defined by the outer surface, wherein the outer surface is 3D-printed. The device may further comprise a heel under the frame.

In another aspect of the disclosure, the channel partially or fully conceals the straps between the inner and the outer surfaces and wherein the frame holds the straps at a desired place at a desired point of attachment according to the user's anatomy; wherein the straps are concealed evenly around the user's part of the body, wherein pressure from the straps are spread evenly, eliminating localized stresses on the frame or on the user.

In a further aspect of the disclosure, the straps are adjusted to secure the user's ankle.

In additional aspects of the disclosure, the device is manufactured from a 3D design file containing the user's anatomic characteristics, wherein the user's anatomic characteristics comprise user specific measurements, scans, casts, or a combination of some or all of these.

In further aspects of the disclosure, a method of fabricating a series of orthopedic or prosthetic custom devices is disclosed, the method comprising: receiving digital data from a 3D design file containing a user's anatomic characteristics; generating a design for an orthopedic or a prosthetic device for the user; 3D-printing the orthopedic or the prosthetic device; wherein user's anatomic characteristics comprise user specific measurements, scans, casts, or a combination of some or all of these.

In another aspect of the disclosure, the user's anatomic characteristics are obtained and provided manually, extracted automatically from a three-dimensional scan and corresponding software, obtained from a physical cast of the user's anatomy, either via manual measurement or a three-dimensional scan of the physical cast, or combination of all or some of these or other methods.

In a further aspect of the disclosure, the orthopedic device is an ankle foot orthosis (AFO) device.

In a further aspect of the disclosure, the device is custom footwear.

In a further aspect of the disclosure, the device is a prosthetic device for upper and lower extremities.

In a further aspect of the disclosure, the device is an orthopedic device selected from the group consisting of, but not limited to, back or spinal braces and supports, elbow splints and braces, finger and thumb splints and braces, hand braces and supports, fracture splints, knee braces and supports, foot braces and supports, toe braces and supports, ankle braces and splints, foot braces and splints, ankle foot orthoses, knee-ankle-foot orthoses, hip-knee-ankle-foot orthoses, hip and thigh splints and braces, shoulder supports and braces, sternum and chest braces and supports, neck braces and supports, orthopedic compression sleeves and garments, mastectomy supports, burn mask orthoses, cranial helmets and combinations thereof.

In a further aspect of the disclosure, the device is custom sports gear, personal protective equipment, luggage, handbags, purses, jewelry, bracelets, or backpacks.

In yet another aspect of the disclosure, a method of fastening straps for orthopedic or prosthetic devices is disclosed, the method comprising: providing a 3D-printed strap channel device having a frame; wherein the frame defines channels between an inner surface and an outer surface of the frame, wherein straps can be threaded through and held in place, wherein the strap channel device is designed according to a user's anatomic characteristics, wherein the device is manufactured from a 3D design file containing the user's anatomic characteristics; attaching the strap channel directly to a user's part of the body or to a user's orthopedic or prosthetic device, threading straps through the channels; securing the straps between the inner and the outer surfaces; wherein the user's anatomic characteristics comprise user specific measurements, scans, casts, or a combination of some or all of these; wherein the strap channel partially or fully conceals the straps within the inner and the outer surfaces and holds the straps at a desired place at a desired point of attachment according to the user's anatomy.

BRIEF DESCRIPTION OF THE DRAWINGS

The accompanying drawings are included to provide a further understanding of the present invention and are incorporated in and constitute a part of this specification. The drawings illustrate exemplary embodiments of the present invention and together with the description serve to further explain the principles of the invention. Other aspects of the invention and the advantages of the invention will be better appreciated as they become better understood by reference to the Detailed Description when considered in conjunction with the accompanying drawings, and wherein.

Figure 1A:
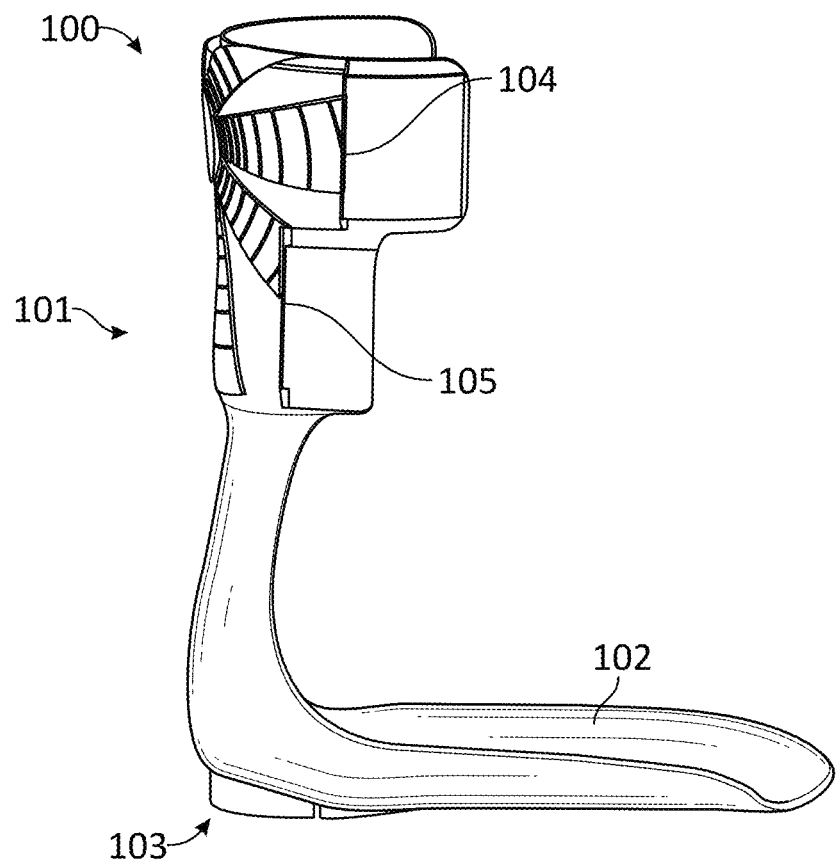
FIG. 1A is a lateral side view of a 3D-printed strap channel for an ankle foot orthotic (AFO) device, according to one embodiment of the present disclosure.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE INVENTION

The following detailed description includes references to the accompanying drawings, which forms a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary, Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. AH such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus. These terms are not meant to limit the elements that they describe, as the various elements may be oriented differently in various applications.

As used herein, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature. Such joining may allow for the transfer of fluids, gasses, and plasma or the flow of electricity or electrical signals.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Embodiments of the present disclosure are directed to orthopedic devices, systems and methods that aim at correcting neuromuscular or skeletal deformities, including those caused by stress to the user's limbs and those which are inherited by the user. The present disclosure is also directed to prosthetic devices, systems and methods that aim at replacing, correcting or supporting a body part or replacing a missing body part.

One embodiment of the present disclosure is a bespoke ankle foot orthosis (AFO) device 100, as shown in FIG. 1A, produced by additive manufacturing (3D-printing) that can be used by a wearer to reduce postural sway and increase postural stability, often prescribed by physicians for their users to be worn bilaterally (on both feet 10), to assist with balance issues and gait instability.

One embodiment of the present disclosure is a 3D-printed strap or fastening system "channel", "tunnel", or "cavity" between an inner and outer surface of a bespoke, ankle foot orthosis (AFO) produced by additive manufacturing (3D-printing) process utilizing a series of user-specific, anatomical measurements. An AFO is an ankle and foot support (brace) that may be worn by an individual to control the foot and ankle, position the foot and ankle, correct foot and ankle deformities, and/or compensate for weakness of the lower limb. The AFO category includes a wide variety of different braces, some prefabricated with general sizing options (i.e. Small, Medium, Large, etc.) and some custom fabricated, designed for specific user anatomies.

In one embodiment the user's measurements may be obtained and provided manually, extracted automatically from a three-dimensional scan and corresponding software, obtained from a physical cast of the user's anatomy, either via manual measurement or a three-dimensional scan of the physical cast, or combination of all or some of these or other methods.

Figure 1B:
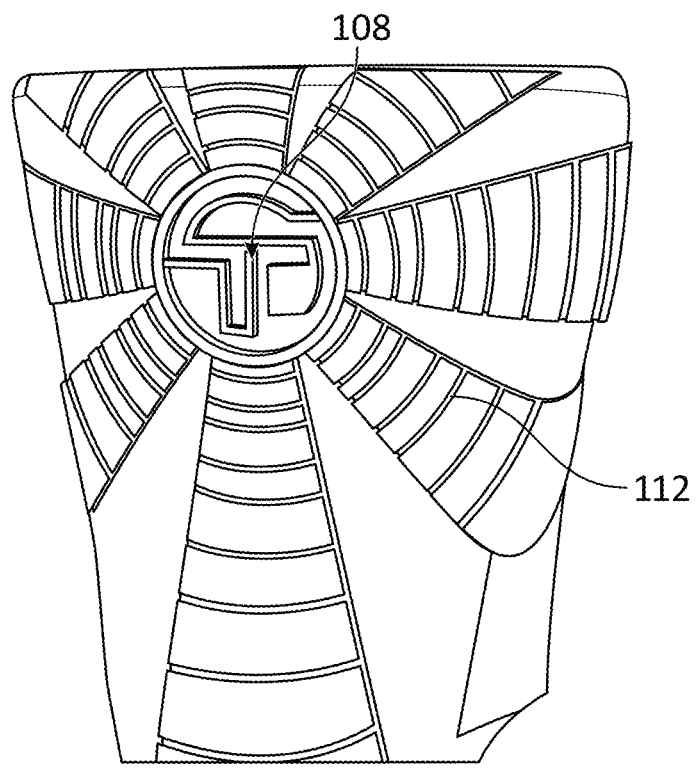
FIG. 1B is an additional lateral side view of the 3D-printed strap channel, according to the present disclosure.
Figure 5:
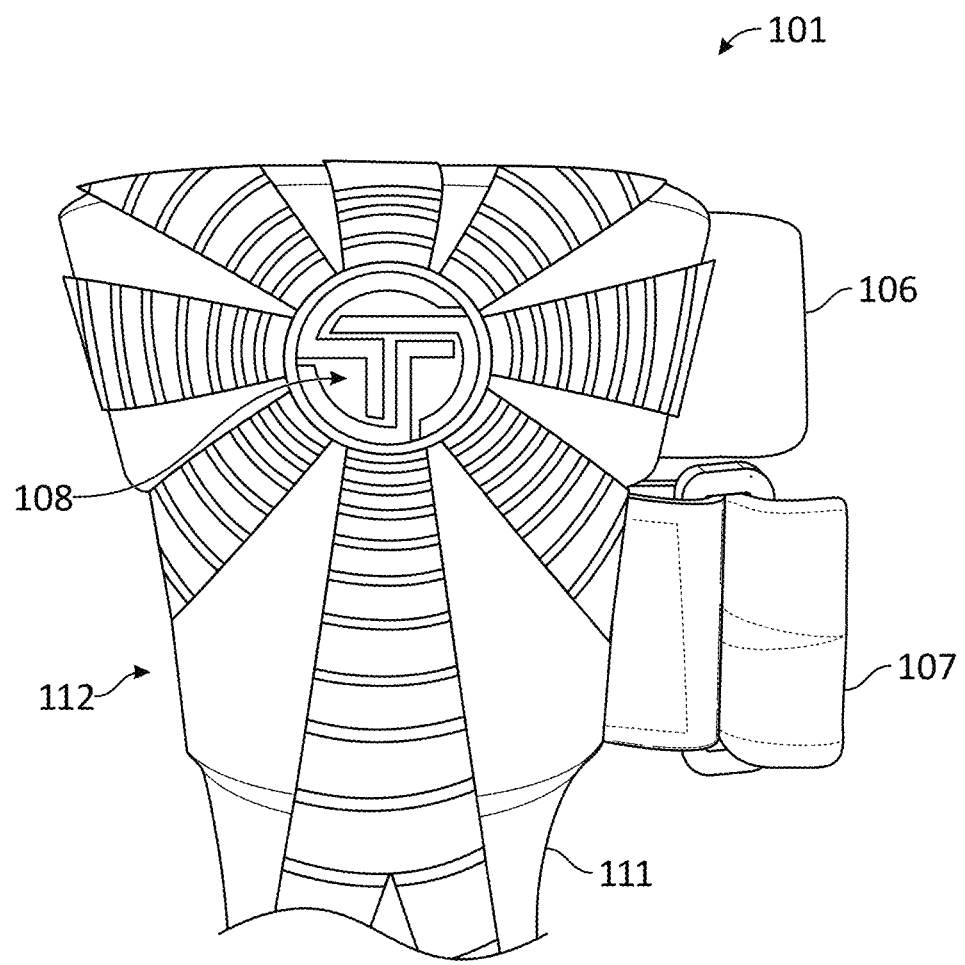
FIG. 5 is a back view of the logo at the upper back of a 3D-printed strap channel with straps, according to one embodiment of the present disclosure.
Figure 6:
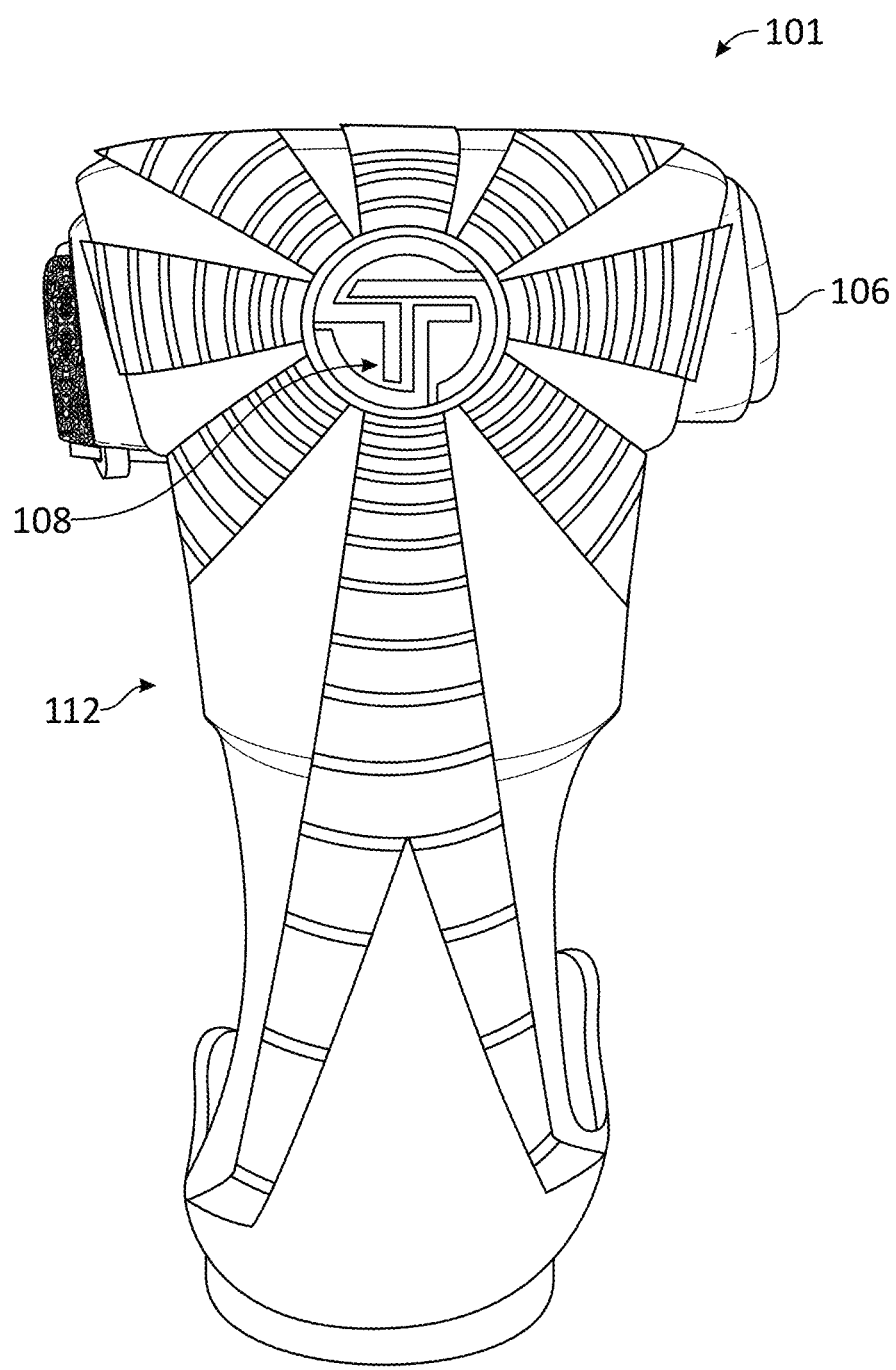
FIG. 6 is another back view of the logo at the upper back of a 3D-printed strap channel, according to one embodiment of the present disclosure.

One embodiment the AFO device 100 comprises a bespoke frame 101 defining a boot 102 where the user's foot 10 will fit in, as shown in FIGS. 1A, 1C, 1D, 7 and 8. The outer surface 111 of the frame 101 is 3D-printed and designed according to the user's anatomic characteristics. The outer surface 111 may define a logo and/or patterns, such as the logo 108 and the sunburst patterns 112 as illustrated in FIGS. 1B, 5 and 6.

In another embodiment AFO 100 may comprise a heel 103 under the sole of the frame, as shown in FIG. 1A. Heel 103 is designed according to the user's corrective needs. In many embodiments AFO 100 comprises at least one 3D-printed channel(s), as shown in FIGS. 1A, 1C, 1D, 2, 3, 4, 5, 6 and 7, defined between an inner surface 109 and an outer surface 111 of the frame 101. The at least one strap channel(s) 104 and 105 are hollow channels defining a space between the inner 109 and the outer 111 surfaces of the frame 101 allowing a strap 106 or fastening system to be inserted through and held in place between the inner and the outer surfaces 109 and 111 of the frame 101, partially or fully concealing the strap 106 or other fastening system between the inner and outer surfaces 109 and 111, and wherein the frame 101 holds the strap in place at the desired point of attachment relative to the user's anatomy supported by the AFO 100. The strap channels 104 and 105 are continuous from a first side 121 of the frame 101 to a second side 123 of the frame 101, wherein the first side 121 of the frame 101 to the second side 123 of the frame 101 defines a semi-curvature or arcuate shape along a body contacting surface designed to generally conform to the shape of a user's body part placed or secured within the frame 101. In one embodiment, the straps 106 or another fastening system are adjusted to secure the user's leg at the ankle level. It is an advantage of the present disclosure and the embodiments described herein that the straps 106 are concealed evenly around the user's part of the body, wherein pressure and tension from the straps 106 are spread evenly, eliminating localized stresses on the frame 101 or on the user during use of the AFO 100.

Figure 1C:
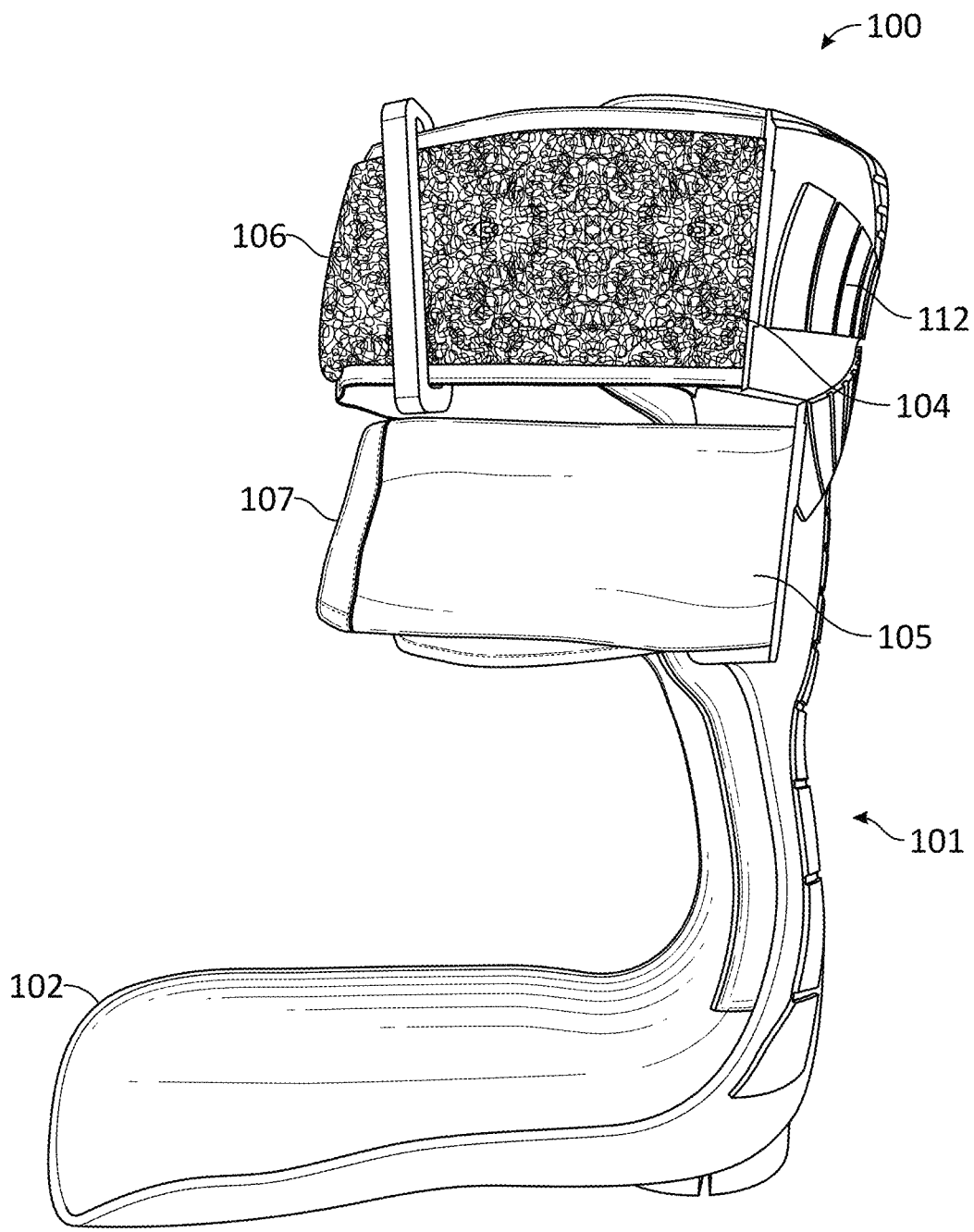
FIG. 1C is a lateral side view of a 3D-printed strap channel for an ankle foot orthotic (AFO) device with strap members according to one embodiment of the present disclosure.

FIG. 1C shows AFO 100 having two adjustable straps 106 secured to the device 100. One of the straps 106 can be referred to as a top adjustable strap 106 and another a lower adjustable strap 107. Strap 106 threads through 3D-printed channel 104 and strap 107 threads through 3D-printed channel 105. The bespoke frame 101 defining the boot 102 where the user's foot 10 will fit in. In one embodiment, the straps 106 and 107 are adjusted to secure the user's leg at the ankle level. It is envisaged that another fastening system may substitute the straps 106.

Figure 1D:
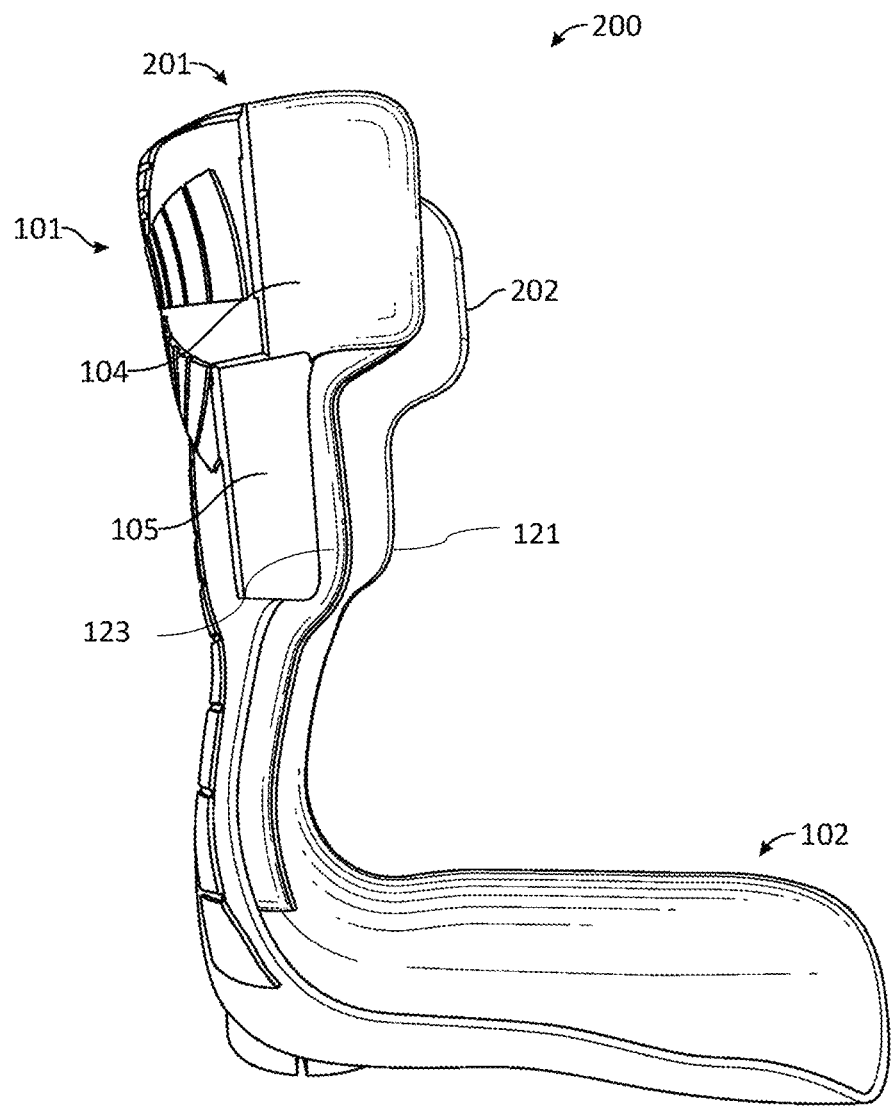
FIG. 1D is another lateral side view of the 3D-printed strap channel without straps, according to the present disclosure.

In another embodiment an AFO device 200 comprises a bespoke frame 101 that can be attached adjacent to a wall of an orthopedic or prosthetic device defining a void 201, wherein the void 201 functions as strap channels, wherein straps or another fastening system can be secured by the channels between the outer surface 111 of the frame 101 and the orthopedic or prosthetic device. FIG. 1D shows the AFO 200 having the frame 101 attached adjacent to a bespoke leg pad 202 defining strap channels 104 and 105. In this embodiment, leg pad 202 works as the inner surface 109. It is envisaged that the bespoke frame 101 can be attached to different orthopedic or prosthetic devices.

Figure 2:
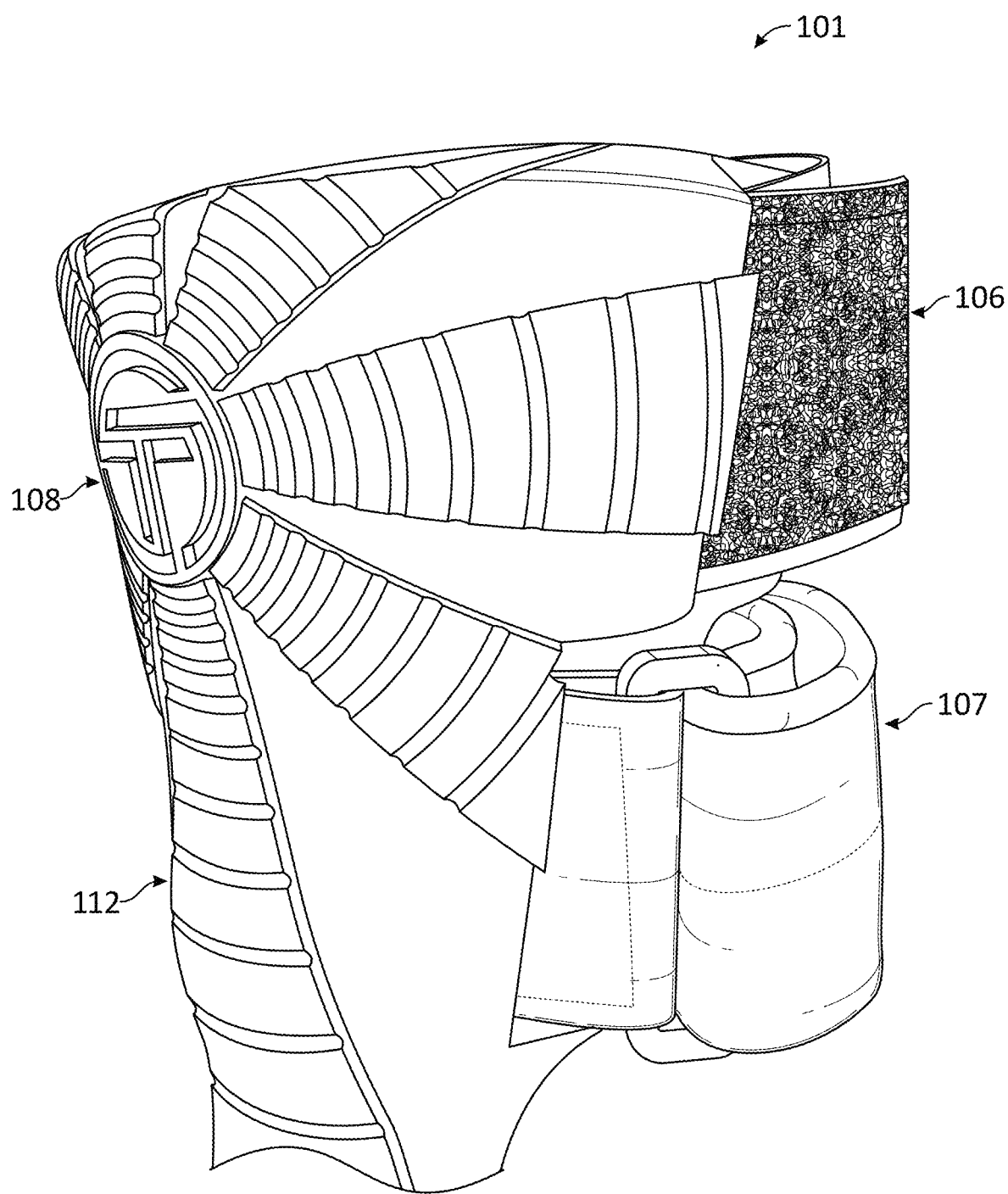
FIG. 2 is a perspective view of the top of a 3D-printed strap channel, according to one embodiment, according to the present disclosure.
Figure 3:
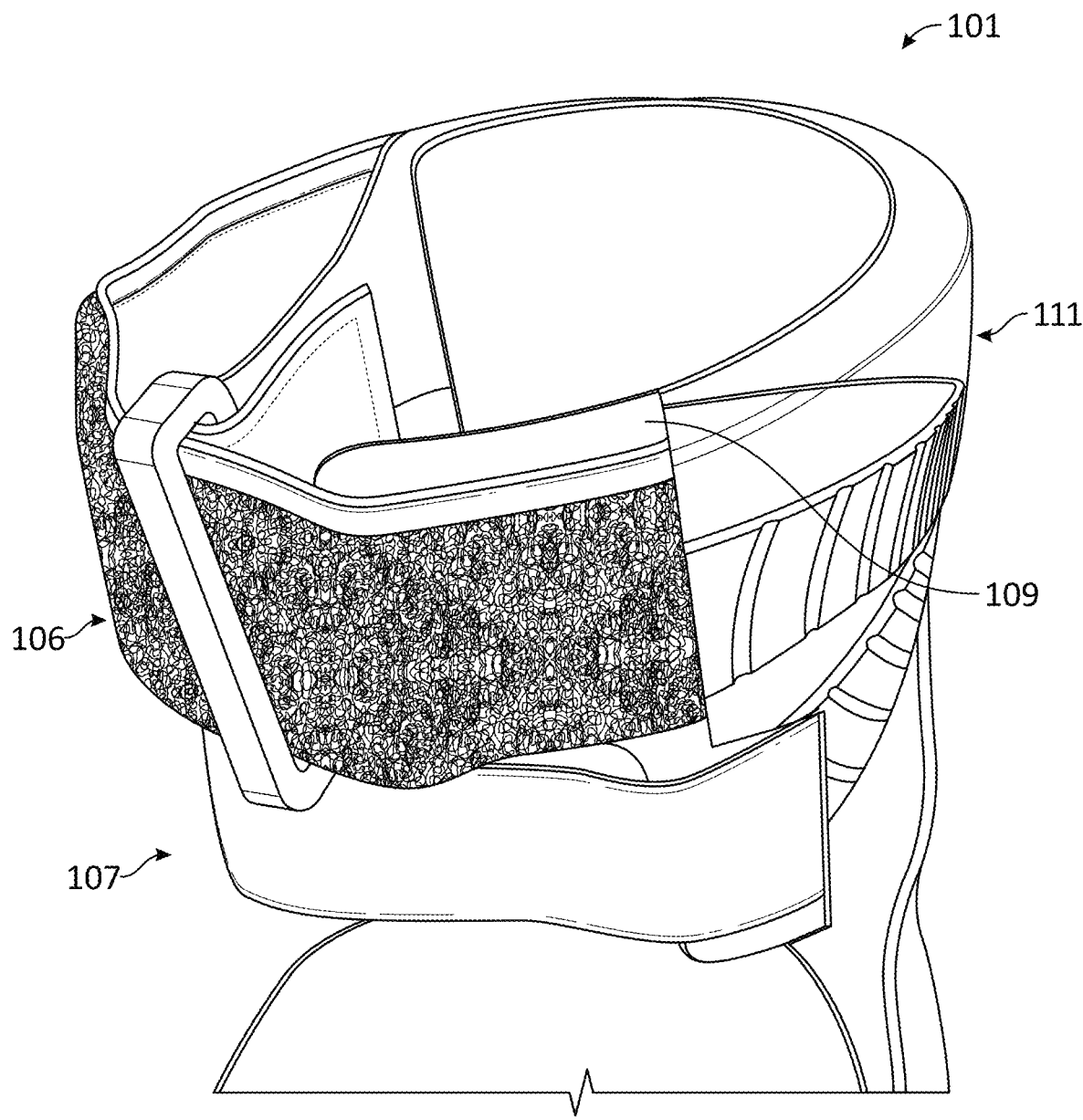
FIG. 3 is another perspective view of the top of a 3D-printed strap channel, according to one embodiment of the present disclosure.

FIG. 2 shows the straps 106 and 107 inserted through and held in place between the inner and outer surfaces 109 and 111 of the AFO 100. FIG. 3 shows another perspective of the straps 106 and 107 inserted through and held in place between the inner and outer surfaces 109 and 111 of the AFO 100.

Figure 4:
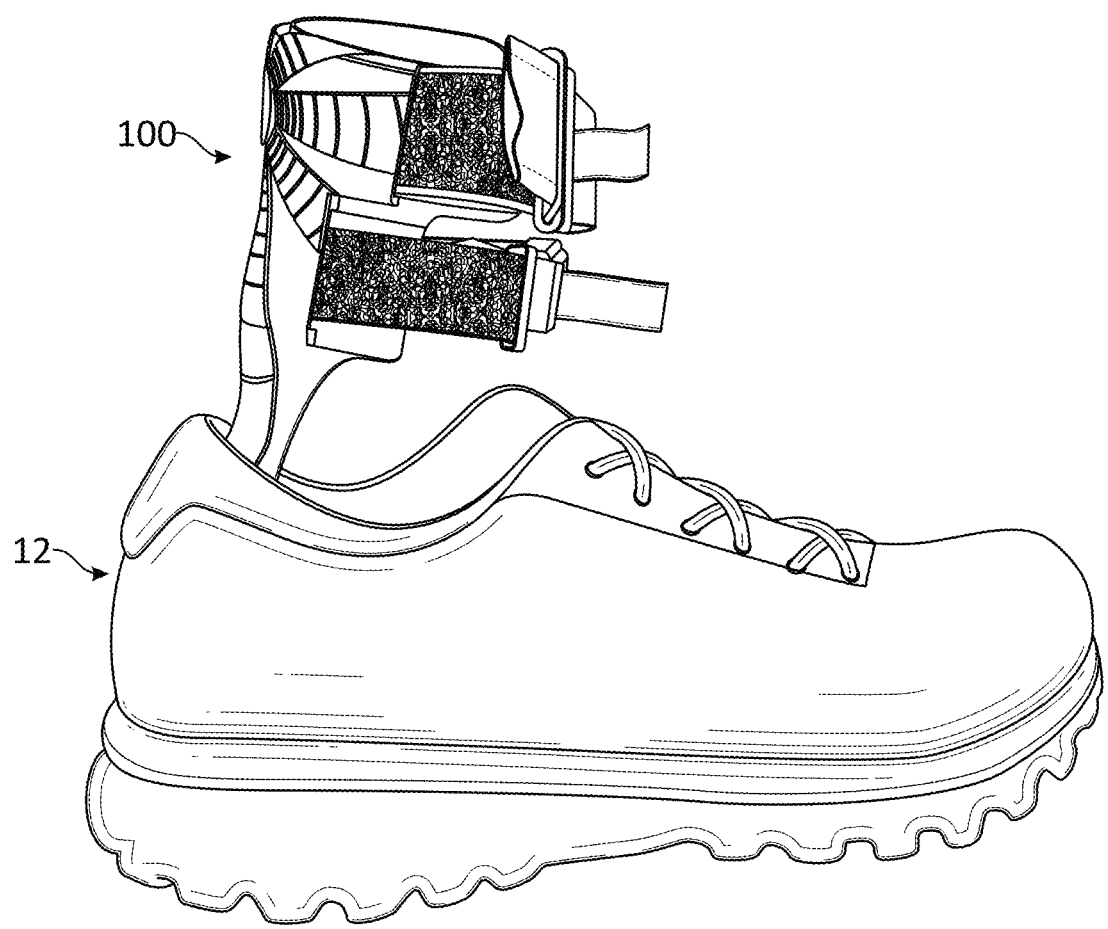
FIG. 4 is a side view of a 3D-printed strap channel at least partially located within a shoe, according to one embodiment of the present disclosure.

FIG. 4 shows AFO 100 having two adjustable straps secured to the device 100. AFO 100 holds a user's foot 10 in a position according to the user's needs and is partially inserted inside a shoe 12, as one embodiment of a method of use of the present disclosure.

FIG. 5 shows the back of the AFO 100, having the straps 106 and 107 inserted through and held in place between the inner and outer surfaces 109 and 111 of the AFO 100. The outer surface 111 of the frame 101 is 3D-printed and designed according to the user's anatomic characteristics. A logo 108 and sunburst patterns 112 are defined by the outer surface 111 of the AFO 100.

In certain embodiments, patterns or designs, such as logo 108 and sunburst patterns 112, may be cut-through the outer or inner surfaces 109 and 111 of the AFO 100 or orthopedic or prosthetic device where such channels 104 and/or 105 are present, exposing the straps 106 and/or 107 that have been inserted through and resting within the inner and outer surfaces 109 and 111 of the device 100 through such design cut-out features, as illustrated in FIGS. 5 and 6.

Because additive manufacturing allows for a bespoke device to be created in such a way, a 3D-printed strap channel design for an AFO device 100, according to one embodiment of the present disclosure, has the following advantages over the traditional means of attaching a strap or fastening system to an AFO or orthopedic or prosthetic device:

A strap or fastening system channel, such as channels 104 and 105, or cavity can be created by 3D printing an inner and outer surface, such as surfaces 109 and 111 of an AFO or orthopedic or prosthetic device whereas the inner and outer surfaces are attached only in areas that do not impede a strap or fastening system from being threaded through such channels, these channels or cavities can be created on a bespoke basis and run through the entire or partial length or width of the device. Such a design minimizes or eliminates the need for additional material costs for items used to secure the straps or fastening system to the device, such as a rivet press, drill, hardware, fabric, soft-goods, hook and loop, glue, and other associated fabrication materials.

Further, A 3D-printed strap channel, such as channels 104 and 105, or cavity can run the entire or partial length or width of an AFO or orthopedic or prosthetic device and adequately hold the strap in place at the desired attachment point to the user's anatomy (for example an ankle or a knee of a user) without the need for additional materials mentioned above, such a design also minimizes the labor costs associated with securing a strap or fastening system to an AFO or orthopedic or prosthetic device utilizing the traditional means mentioned above.

Still further, A 3D-printed strap channel, such as channels 104 and 105, or cavity can run the entire or partial length or width of an AFO or orthopedic or prosthetic device in any direction and partially or fully enclose the strap(s) or fastening system(s) within an inner and outer surface of the device, such as surfaces 109 and 111, a 3D printed strap channel on an AFO or orthopedic or prosthetic device can adequately hold the strap or fastening system in place at the desired point of attachment of the user's anatomy without allowing the strap to hang down or become accidentally detached from the device. By securing the strap between the inner and outer surface of a device, wear and tear associated with straps hanging and dragging on the floor when not in use, such as common with traditional means of securing a strap or fastening system to a device, are minimized, or eliminated. Furthermore, because partially or fully enclosing a strap or fastening system in this manner, between an inner and outer surfaces of an AFO or orthopedic or prosthetic device, is better able to hold the strap in place at the desired and intended location for securing the device to the user's anatomy over traditional means, users with dexterity issues are able to better access, grab, manipulate, and secure the straps or fastening system to their anatomy.

The integrated channel of the device 100, such as channels 104 and 105, that go around the device/body part spreads the pressure from the strap to the device over a much larger area when compared to a conventional strapping system, where, for example, a D-ring is attached with a rivet or a screw to the frame/shell creating significant localized stresses on the shell material leading to breakage and failure.

The use of additive manufacturing allows for a strap channel, such as channels 104 and 105, or cavity to be created on a bespoke basis between an inner and outer surface, such as surfaces 109 and 111, of an AFO or orthopedic or prosthetic device, whereas the inner and outer surfaces are attached in way and in such locations of the device, where such cavities between the inner and outer surfaces are left unimpeded in the direction through which the strap or fastening system may be inserted through, such a design has aesthetic and commercial advantages over fastening a strap by traditional means. By partially or fully concealing the strap within an inner and outer surface of an AFO or orthopedic or prosthetic device, such designs can minimize or eliminate the unsightly appearance of straps, hardware, soft goods, etc. that are left exposed on the inner and/or outer surface of an AFO when the strap is attached by traditional means referenced above. By partially or fully concealing the straps or fastening system within the frame ("body") of the AFO or orthopedic or prosthetic device, the designer has more liberty to create and implement unique design features, such as the logo 108 and the sunburst patterns 112, on the outer or inner surface of the AFO or orthopedic or prosthetic device without such features being partially or fully covered by straps, hardware, soft goods, etc. attached to a device by traditional means. Furthermore, partially or fully concealing the strap or fastening system between an inner and outer surface of an AFO or orthopedic or prosthetic device allows for a unique design opportunity to cut a pattern, words, images, logos, or other design feature through the outer surface of the AFO or orthopedic or prosthetic device in the area where the strap is threaded between the inner and outer surface of the device, therefore exposing the strap that is positioned between the inner and outer surface, where such a design cut-through is present on the outer surface of the device. Such a cut-through design feature on the outer or inner surfaces of a 3D-printed AFO or orthopedic or prosthetic device where a strap channel, such as channels 104 and 105, is present has the added benefit of allowing additional access points for powder clearance from such a channel or cavity. Without adequate access to such a channel, powder used in the additive manufacturing process can build up and remain within such a cavity, causing the strap or fastening device to be exposed to and soiled by such powder In addition to the design and powder clearance advantages mentioned above, such a 3D-printed channel feature for an AFO or orthopedic or prosthetic devices allows for a distinct and unique aesthetic for all devices utilizing such a feature within a brands additive manufacturing product catalog, enhancing the brands commercial appeal.

It is to be understood that the systems and methods of designing and fabricating the bespoke devices described in this application can be used for custom design and fabricate several devices in several different fields. For example: a) custom footwear, including sneakers, sandals, boots, high heels, etc; b) prosthetic device for upper and lower extremities, etc; c) orthopedic devices, including back braces, fracture splints, knee braces, ankle braces, cranial helmets, etc; d) sports gear, including helmets, shin guards, hockey pads, inline skates, snowboarding/ski boots, football padding, etc; e) costumes, including masks, helmets, padding, etc; e) personal protective equipment, including face shields, masks, googles, etc; f) other accessories, including luggage, handbags, purses, jewelry, bracelets, backpacks, etc.

FIG. 6 shows the back of the AFO 100, having only the top strap 106 inserted through and held in place between the inner and outer surfaces 109 and 111 of the AFO 100. The outer surface 111 of the frame 101 is 3D-printed and designed according to the user's anatomic characteristics. A logo 108 and sunburst patterns 112 are defined by the outer surface 111 of the AFO.

Figure 7:
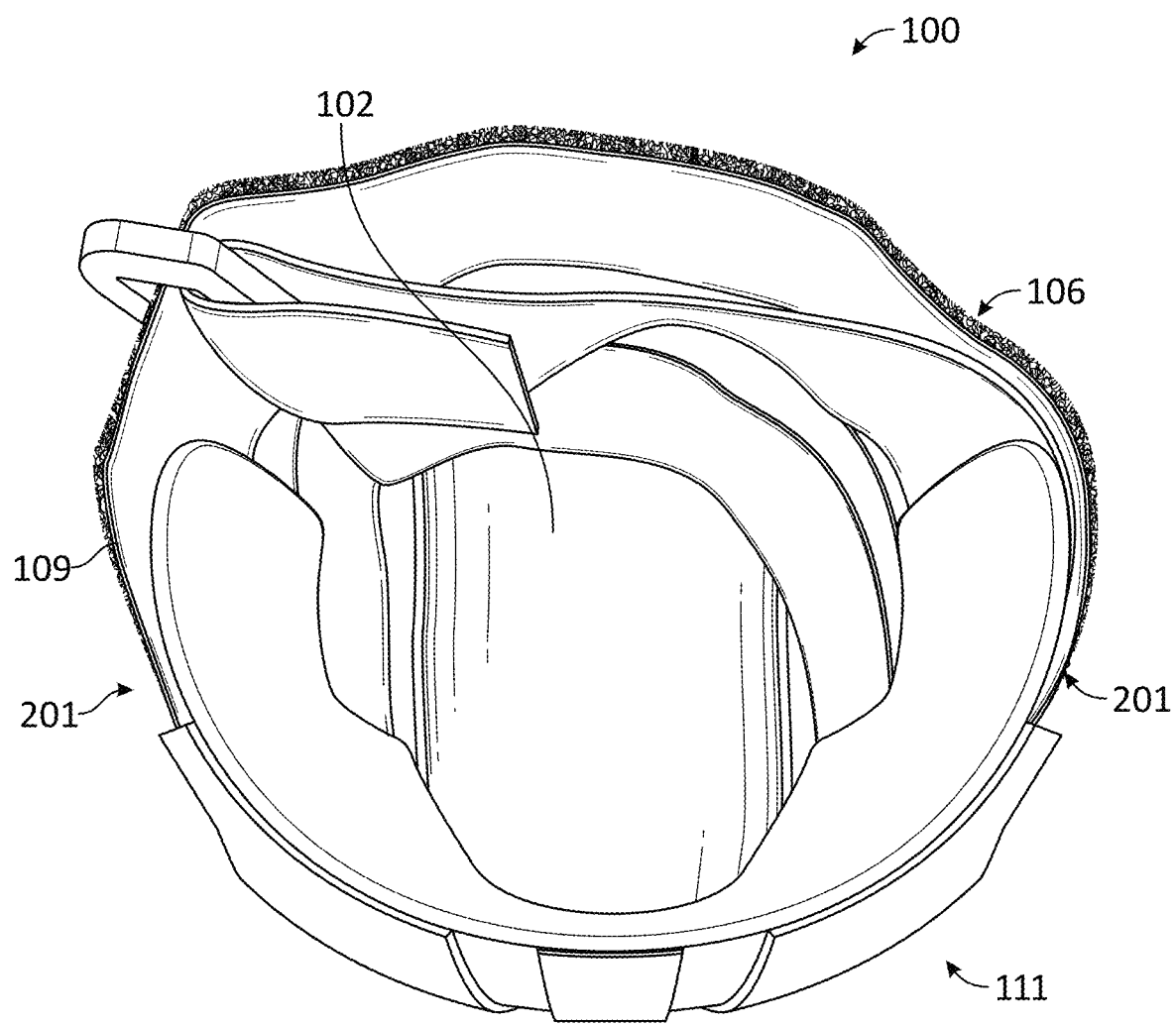
FIG. 7 is a top view of the top of the 3D-printed strap channel, according to one embodiment of the present disclosure.

FIG. 7 shows the top of the AFO 100, having the straps 106 and 107 inserted through and held in place between the inner and outer surfaces 109 and 111 of the AFO 100. The bespoke frame 101 defining a boot 102 where the user's foot 10 will fit in. The frame 101 also defines a void 201 between the inner and the outer surfaces 109 and 111, wherein the void 201 functions as a strap channel. Strap channels 104 and 105 are hollow channels defined between the inner 109 and the outer 111 surfaces of the frame 101. The straps 106 and 107 are threaded through the strap channels 104 and 105 and held between the inner and the outer surfaces 109 and 111. In this embodiment shown in FIG. 1, the straps 106 and 107 are adjusted to secure the user's leg at the ankle level. It is envisaged that another fastening system may substitute the straps.

Figure 8:
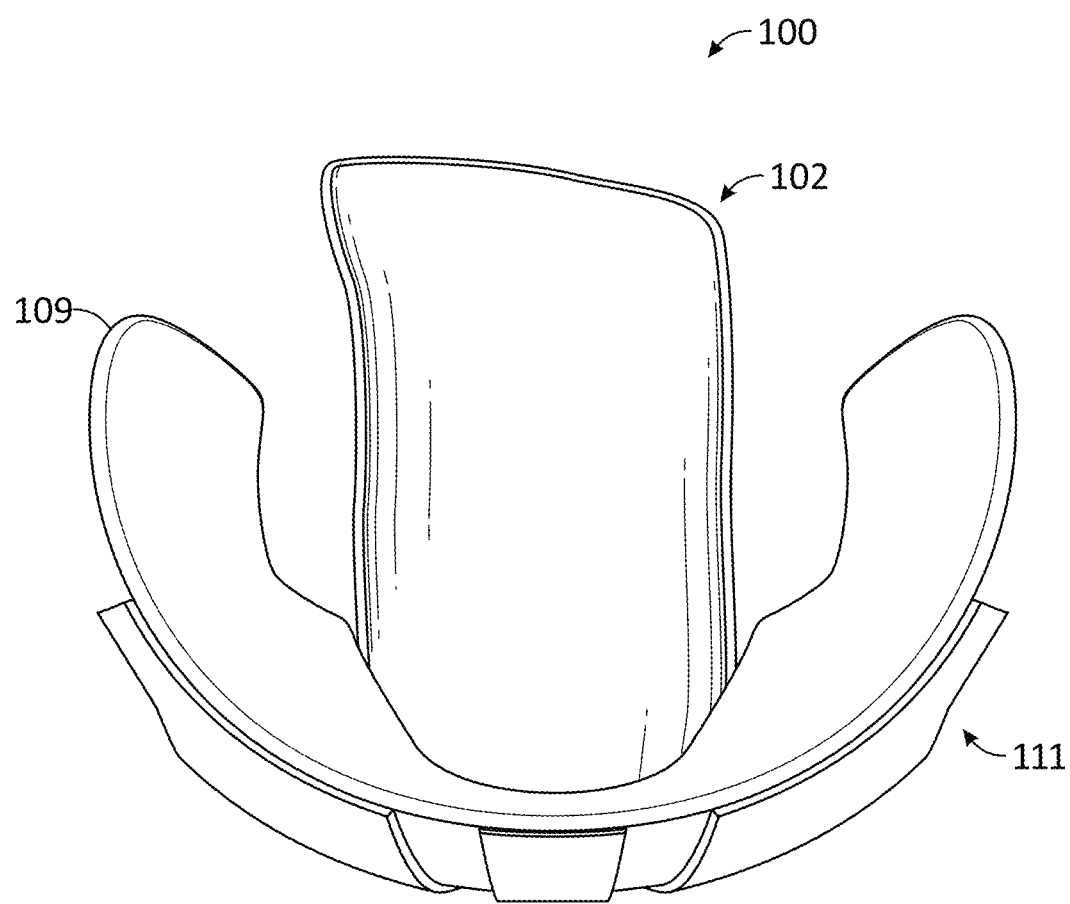
FIG. 8 is another top view of the top of the 3D-printed strap channel, according to one embodiment of the present disclosure.

FIG. 8 shows the top of the AFO 100 having the 3D-printed channels 104 and 105 without the straps.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. An additive manufactured device defining a first channel for the placement of a first strap for an ankle foot orthotic (AFO), the additive manufactured device comprising: a frame, the frame having an inner surface and an outer surface, and a space between the inner surface and the outer surface defining the first channel, wherein the first channel is an entirely hollow channel defined between the inner and the outer surfaces of the frame; wherein a first side of the frame to a second side of the frame defines a semi-curvature shape configured to hold a user's ankle and foot portion; wherein the first strap can be threaded through the first channel, wherein the first channel is continuous along a length of the first side of the frame, and wherein a portion of the first strap is fully enclosed within the first channel between the first side of the frame and the second side of the frame; wherein the first strap is adjusted and configured to secure the user's ankle and the first channel reduces wear to a portion of the first strap enclosed within the first channel from exterior elements; wherein the first channel is 3D-printed and designed according to a user's anatomic characteristics; and the frame further comprising a second channel formed between the first side of the frame and the second side of the frame, wherein a second strap can be threaded through the second channel, wherein the second channel is 3D-printed and designed according to the user's anatomic characteristics, wherein a portion of the second strap is fully enclosed within the first channel between the first side of the frame and the second side of the frame.

2. The additive manufactured device of claim 1, wherein the first channel at least partially conceals the first strap between the inner and the outer surfaces and wherein the frame holds the first strap at a desired place at a desired point of attachment according to the user's anatomy.

3. The additive manufactured device of claim 2, wherein the first strap is concealed evenly around the additive manufactured device, wherein pressure from the first strap is spread evenly eliminating localized stresses on the frame or on the user.

4. The additive manufactured device of claim 1, wherein the additive manufactured device is manufactured from a 3D design file containing the user's anatomic characteristics.

5. The additive manufactured device of claim 4, wherein the user's anatomic characteristics comprise user specific measurements, scans, casts, or a combination of some or all of these.

6. The additive manufactured device of claim 1, wherein a logo is defined by the outer surface, wherein the outer surface is 3D-printed on the inner surface or on the outer surface; or a negative of the logo is cut-through the inner surface or the outer surface where the first channel is present, wherein the cut through exposes the first channel or first strap that sits between the inner surface and the outer surface.

7. The additive manufactured device of claim 1, wherein at least one pattern is defined by the outer surface, wherein the outer surface is 3D-printed on the inner surface or on the outer surface; or a negative of the pattern is cut-through the inner surface or the outer surface where the first channel is present, wherein the cut through exposes the first channel or strap that sits between the inner surface and the outer surface.

8. The additive manufactured device of claim 1, wherein the additive manufactured device further comprises a heel positioned at an underside of the second side of the frame.

9. A method of fastening one or more straps for orthopedic or prosthetic devices, the method comprising: providing a 3D-printed strap channel device having a frame; wherein the frame defines a first channel between an inner surface and an outer surface of the frame, wherein a first strap can be threaded through and held in place within the first channel, wherein the 3D-printed strap channel device is designed according to a user's anatomic characteristics, wherein the orthopedic or prosthetic devices is manufactured from a 3D design file containing the user's anatomic characteristics; wherein a first side of the frame to a second side of the frame defines a semi-curvature shape configured to hold a user's ankle and foot portion; wherein the first channel is continuous along a length of the first side of the frame; wherein a portion of the first strap is fully enclosed within the first channel between the first side of the frame and the second side of the frame; attaching the first strap through the first channel directly to the posterior portion of the user's ankle; threading a second strap through a second channel; and securing the first strap and second strap between the inner and the outer surfaces around the user's ankle.

* * * * *